(12) United States Patent
Liao et al.

(10) Patent No.: US 7,843,635 B2
(45) Date of Patent: Nov. 30, 2010

(54) DEVICE FOR TRAPPING OR STRETCHING MICROSCOPIC SUBSTANCE AND METHOD THEREOF

(75) Inventors: Guan-Bo Liao, Taipei (TW); Chi-Hung Lin, Taipei (TW); Arthur Chiou, Taipei (TW)

(73) Assignee: National Yang-Ming University, Taipei (TW)

( * ) Notice: Subject to any disclaimer, the term of this patent is extended or adjusted under 35 U.S.C. 154(b) by 242 days.

(21) Appl. No.: 11/764,433

(22) Filed: Jun. 18, 2007

(65) Prior Publication Data
US 2008/0310009 A1    Dec. 18, 2008

(51) Int. Cl.
G02B 13/10 (2006.01)
G02F 1/33 (2006.01)

(52) U.S. Cl. ........................ 359/433; 359/305

(58) Field of Classification Search ............... 359/368, 359/385, 388, 433, 305, 308, 309, 290, 291; 250/234–236, 201.3, 458.1
See application file for complete search history.

(56) References Cited

U.S. PATENT DOCUMENTS

| | | | | |
|---|---|---|---|---|
| 6,532,071 B2* | 3/2003 | Zare et al. | ................. | 356/437 |
| 6,740,868 B1* | 5/2004 | Knebel et al. | ................ | 250/234 |
| 7,133,188 B2* | 11/2006 | Johnson | ..................... | 359/311 |
| 7,397,596 B2* | 7/2008 | Yacoubian | ................... | 359/290 |
| 7,480,045 B2* | 1/2009 | Kung et al. | ................. | 356/311 |
| 2004/0256542 A1 | 12/2004 | Okazaki | | |
| 2007/0008528 A1 | 1/2007 | Lin | | |

OTHER PUBLICATIONS

J. Guck, R. Ananthakrishnan, H. Mahmood et al., "The optical stretcher: a novel laser tool to micromanipulate cells," Biophysical journal 81 (2), 767-784 (2001).

M. J. Lang, C. L. Asbury, J. W. Shaevitz et al., "An automated two-dimensional optical force clamp for single molecule studies," Biophysical journal 83 (1), 491-501 (2002).

Sylvie Henon, Guillaume Lenormand, Alain Richert et al., "A New Determination of the Shear Modulus of the Human Erythrocyte Membrane Using Optical Tweezers," Biophysical journal 76, 1145-1151 (1999).

J. A. Dharmadhikari, S. Roy, A. K. Dharmadhikari et al., "Natually occurring, optically driven,cellular rotor," Appl. Phys. Lett 85, 6048-6050 (2004).

J. A. Dharmadhikari, S. Roy, A. K. Dharmadhikari et al., "Torque-generating malaria infected red blood cells in an optical trap," Opt. express (2004).

(Continued)

Primary Examiner—Timothy J Thompson
Assistant Examiner—Tuyen Q Tra
(74) Attorney, Agent, or Firm—WPAT, P.C.; Anthony King

(57) ABSTRACT

The present invention provides a device for trapping or stretching a microscopic substance comprising (a) a light source; (b) an acousto-optic modulator (AOM); (c) a beam-expander; (d) an object lens; and (e) an incoherent light source. The present invention further provides a method for trapping or stretching a microscopic substance comprising (a) providing a focused laser beam to form a focal spot and (b) scanning a plurality of points on said microscopic substance by said focal spot by way of the AOM.

19 Claims, 3 Drawing Sheets

OTHER PUBLICATIONS

Jochen Guck, Stefan Schinkinger, Bryan Lincoln et al., "Optical Deformability as an Inherent Cell Marker for Testing Malignant Transformation and Metastatic Competence," Biophysical journal 88, 3689-3698 (2005).

Arthur Ashkin, "Optical trapping and manipulation of neutral particles using lasers," Proc. Natl. Acad. Sci. USA vol. 94, pp. 4853-4860, May (1997).

John Sleep, David Wilson, Robert Simmons, and Walter Gratzer, "Elasticity of the Red Cell Membrane and Its Relation to Hemolytic Disorders: An Optical Tweezers Study," Biophysical Journal vol. 77 Dec. 1999 3085-3095.

Jana Jass et al., "Physical Properties of *Escherichia coli* P Pili Measured by Optical Tweezers," Biophysical Journal vol. 87 Dec. 2004 4271-4283.

\* cited by examiner

DEVICE FOR TRAPPING OR STRETCHING MICROSCOPIC SUBSTANCE AND METHOD THEREOF

FIELD OF THE INVENTION

The present invention relates to a device for trapping or stretching microscopic substance and method thereof.

DESCRIPTION OF PRIOR ART

The visco-elastic property of cells in response to external mechanical stimuli has been probed by several methods. For example, the application of a sharp tip directly onto the cell membrane or pulling a small bead adhered to the cell membrane leads to a relatively localized deformation. Over the past three decades, it has been found that laser can be utilized to capture and manipulate particles and cells with diameters on the order of a micron to tens of microns. The technologies of laser traps or laser tweezers were developed employing laser light to trap or move microscopic substances, which are extremely difficult to move or manipulate by traditional tweezers, to desired positions.

The basic physical principle of manipulating microscopic substances by laser light can be explained by regarding the light beam as a stream of photons each bearing a specific amount of momentum and that the change in momentum as the photons are either reflected or refracted by the substance is converted into force on the particle. Under appropriate conditions, the net optical forces can form a three-dimensional potential well to stably confine a microscopic substance within a small volume.

Common laser trap devices fall into two categories. One is the single-beam gradient force optical trap, which is also known as laser tweezers or optical tweezers. It employs a strongly focused laser beam to form a three-dimensional potential well, capable of attracting and confining a dielectric particle in the vicinity of the focal spot of the laser beam. Laser tweezers enable us to actively manipulate micro-and nano-particles and to accurately move the particles non-invasively from one point to another. Optical tweezers with near-infrared laser (e.g. $\lambda$=1064 nm) have been demonstrated for non-invasive trapping and manipulation of single living cell since 1987. The technology is widely used in various fields of research, laser tweezers can be used to capture and trap cells, investigating dynamics of microtubules, mobile behaviors and characteristics of motor proteins such as dynein and kinesin thereof, studying swimming movements of sperms, and investigating polymerization properties of DNA. In addition, laser tweezers contribute greatly to advances in physical and chemical researches, especially in colloid and interface sciences.

With proper force calibration, optical tweezers can be used as a convenient force transducer for the measurement of biological molecular interactions. Optical tweezers have also been used for the study of cellular visco-elastic property. For example, Bronkhorst et al. used multi-beam optical tweezers to bend discotic red blood cells (RBCs) and measured the recovery time in 1995. Sylvie Hénon et al. used optical tweezers to measure the RBC elasticity coefficient in 1999 in which two small silica beads were adhered to opposite faces of a RBC to serve as handles for optical trap. The cell was seized and deformed by trapping the beads in twin optical tweezers and increasing the distance between the two focal spots. Rotation of a trapped RBC using a polarized laser beam was demonstrated by J. A. Dharmadhikari et al. in 2004. Furthermore, they demonstrated that torque-generating is different between a malaria infected red blood cell and a normal RBC.

However, the major disadvantage of using optical tweezers for trapping is that the highly focused laser beam will damage the trapped biological substances such as cells or DNA, causing substantial losses of some intrinsic properties of the substance. In addition, single-beam optical tweezers without other auxiliaries can not be used in stretching the microscopic substance for further investigation of the visco-elastic properties.

An alternative for optical micromanipulation is a counter-propagating dual-beam trap, which is also known as optical stretcher, in which a particle is illuminated from two opposite sides by two co-linear laser beams propagating along opposite directions, generating optical pressure on the surface of the particle and causing optical trapping and stretching. If the particle, for example, a cell, is flexible, it will be stretched and will deform in the direction along the optical axis. The optical stretcher in a fiber-optical dual-beam trap leads to a relatively more uniform force distribution over the whole cell, and hence a more uniform deformation. In 2001, Guck et al. used a fiber-optical dual-beam trap to trap and stretch RBCs for non-invasive study of the visco-elastic property of a single RBC in buffer solution. Furthermore, measurements of the elastic-coefficients of normal, cancerous, and metastatic breast epithelial cells by optical stretcher indicated that the elastic-coefficients may serve as an inherent cell maker that offers a sensitive cellomic alternative to current proteomic techniques. In the observations of cells such as human red blood cells and mice fibroblasts, it is discovered that the extent of deformation differs with the cell types. Moreover, since the laser beams in the dual-beam optical stretcher were diverging Gaussian beams exiting from single-mode fibers, the probability and extent of potential radiation damage to the trapped particle was significantly reduced.

Nevertheless, due to the use of non-focused laser beam and the opposite direction of the counter-propagating laser beams, the high power and high precision were inevitably required in the optical stretcher. In addition, the substance should be pre-treated to meet the requirement for the symmetry. The mechanical vibration generated from the operation also reduces the overall stability of optical stretcher system.

In light of the above drawbacks of one-beam optical tweezers and dual-beam optical stretchers, an improved optical manipulation tool which would not damage the substance and has no need of pre-treatment with lower requirement for power and precision was in an urgent and critical demand.

US patent publication No. 2004256542 disclosed an optical tweezers device. US patent publication No. 2007/0008528 provided a device and method for simultaneous optical trapping, stretching, and real-time detection and measurement for morphological deformation of micro-particles.

SUMMARY OF THE INVENTION

The present invention provides a device for trapping or stretching a microscopic substance comprising (a) a light source for irradiating laser beam; (b) an acousto-optic modulator (AOM) for regulating the direction of said laser beam irradiating from said light source; (c) a beam-expander for expanding and collimating the light beam emitting from said AOM; (d) an object lens for focusing the laser beam passing through said beam-expander; and (e) an incoherent light source for imaging said microscopic substance.

The present invention further provides a method for trapping or stretching a microscopic substance comprising (a)

providing a focused laser beam to form a focal spot and (b) scanning a plurality of points on said microscopic substance by said focal spot by way of the AOM.

DESCRIPTION OF MAJOR PARTS IN THE PRESENT INVENTION

Figure 1:
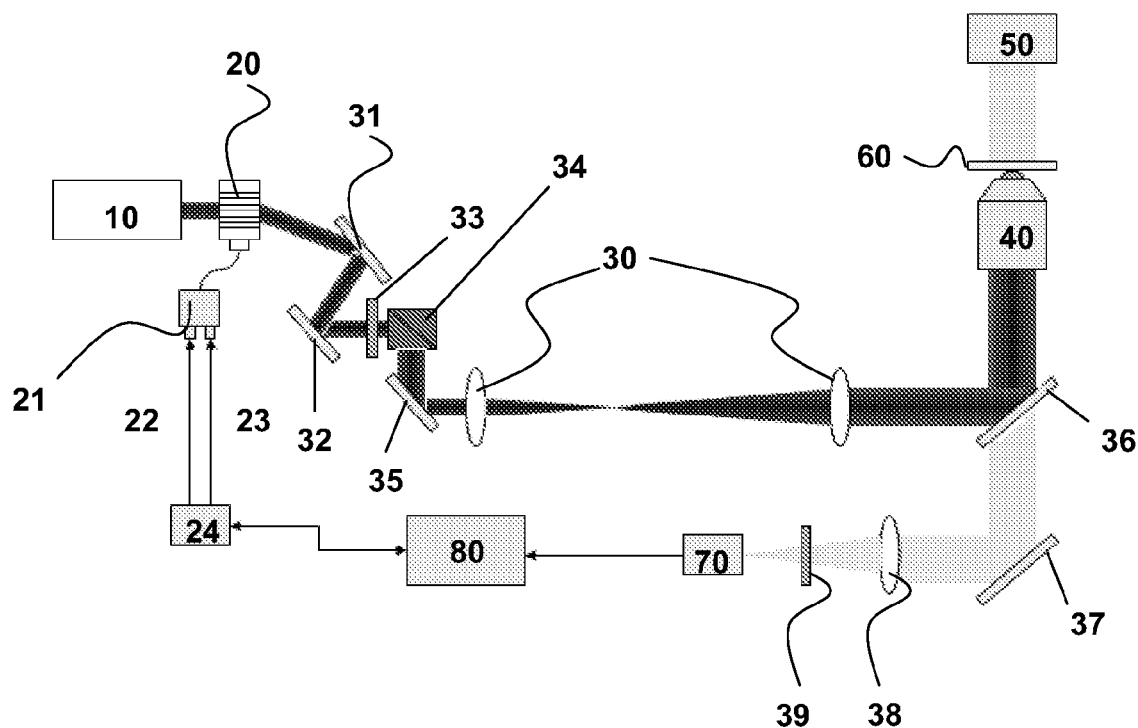
FIG. 1 shows a schematic diagram of an oscillatory optical tweezers for trapping or stretching microscopic substance of the present invention.
Figure 2:
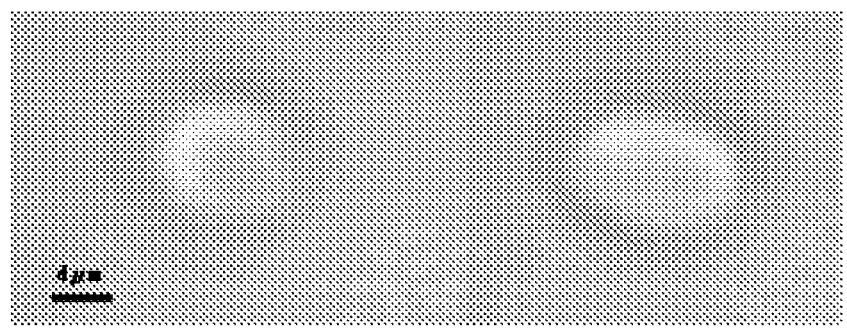
FIG. 2 shows an incoherent image of a spherical RBC trapped by conventional stationary one-beam optical tweezers (the left panel) and the image of the same RBC trapped and stretched by the oscillatory optical tweezers provided by the present invention (the right panel). The scanning frequency=1 k Hz and scanning distance=9.4 μm.
Figure 3:
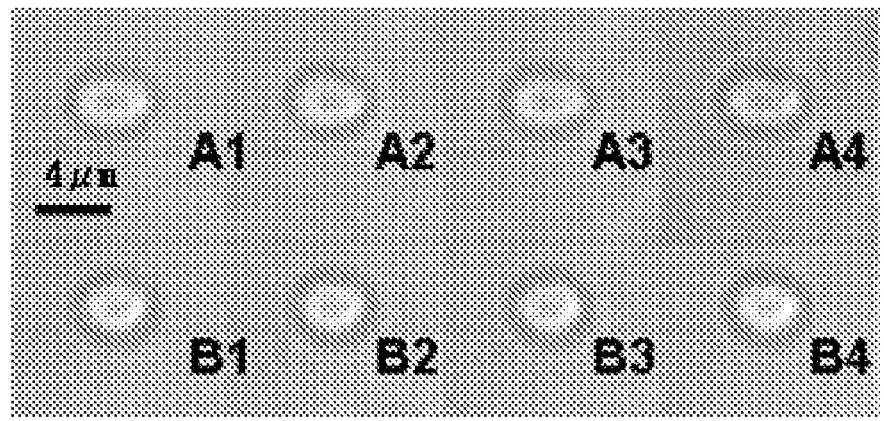
FIG. 3 indicates the incoherent image of a liposome sample trapped and stretched by the oscillatory optical tweezers provided by the present invention with oscillation frequency=1 k Hz and scanning distance=2.88 μm. A: discrete scanning; B: continuous scanning. The images were taken at the steady state by alternately switching between the two scanning modes sequentially in the order of A1, B1, A2, B2, etc.

- 10: Light source for laser beam illumination
- 20: Acousto-optic modulator (AOM)
- 21: Radio frequency
- 22: Modulation voltage $V_T$
- 23: Modulation voltage $V_{MOD}$
- 24: Data acquisition card (DAQ card)
- 30: Beam-expander
- 31: Mirror 1
- 32: Mirror 2
- 33: λ/2 wave plate
- 34: Polarization beam split cube
- 35: Mirror 3
- 36: Mirror 4
- 37: Mirror 5
- 38: F=10 cm object lens
- 39: Filter
- 40: Object lens
- 50: Incoherent light source
- 60: Stage
- 70: Charge Coupled Device (CCD) camera
- 80: Computer

DETAILED DESCRIPTION OF THE INVENTION

Term Definition

Acousto-Optic Modulator (AOM)

An acousto-optic modulator (AOM), also called a Bragg cell, uses the acousto-optic effect to diffract and shift the frequency of light using sound waves (usually at radio-frequency). They are used in lasers for Q-switching, telecommunications for signal modulation, and in spectroscopy for frequency control. Acousto-optic modulators are much faster than typical mechanical devices such as tiltable mirrors. The time it takes an AOM to shift the exiting beam in is roughly limited to the transit time of the sound wave across the beam (typically 5 to 100 microseconds). This is fast enough to create active modelocking in an ultrafast laser. When faster control is necessary electro-optic modulators are used. However, these require very high voltages (e.g. 10 kilovolts), whereas AOMs offer more deflection range, simple design, and low power consumption (<3 watts).

Microscopic Substance

The microscopic substance in the present invention stands for substance that has a diameter ranged from 60 nm to 20 μm.

Focusing

In the present invention, the laser beam used for trapping or stretching microscopic substances is focused by an object lens, forming a focal spot on the microscopic substance. Such a process is termed as focusing and the laser beam emitting from the object lens is termed as focused laser beam in the present invention.

Scanning

By rapidly changing the direction of the focused laser beam, the focal spot on the microscopic substance would not rest in one site but keep moving on the substance along a particular path. Such a process is termed as scanning in the present invention. The damaging effect generated from the laser beam on the substance can be significantly scattered to a harmless level via the scanning process.

The present invention provides a device for trapping or stretching a microscopic substance comprising (a) a light source for irradiating laser beam; (b) an acousto-optic modulator (AOM) for regulating the direction of said laser beam irradiating from said light source; (c) a beam-expander for expanding and collimating the light beam emitting from said AOM; (d) an object lens for focusing the laser beam passing through said beam-expander; and (e) an incoherent light source for imaging said microscopic substance.

In the preferred embodiment, the microscopic substance manipulated by the present invention has a diameter ranged from 60 nm to 20 μm. In the more preferred embodiment, the microscopic substance has a diameter ranged from 1 μm to 12 μm. In the most preferred embodiment, the microscopic substance has a diameter ranged from 4 μm to 5 μm.

The AOM in the present invention not only regulates the direction of laser beam but further regulates the scanning frequency or intensity of said laser beam. By precise controlling of above three parameters, one can finely tune the optical tweezers device to meet the experimental needs and obtain more accurate information derived from operation. In the present invention, the AOM is controlled by modulation voltage $V_T$ and $V_{MOD}$, where $V_T$ controls diffraction angle of laser beam and $V_{MOD}$ controls diffraction power angle of laser beam.

The device provided by the present invention further comprises a Charge Coupled Device camera for imaging the microscopic substance. The CCD camera in the present invention can be replaced by other electronic element which converts the optical signals to electronic signals.

The device provided by the present invention further comprises a computer for imaging the microscopic substance and processing the obtained data relating to the microscopic substance. Via the combination of the present invention and the computer, real-time observation of the micromanipulated substance can be realized.

When using the conventional optical tweezers to manipulate biological substances such as cells, the high power and high frequency of laser beam would adversely alter the biological activity of the substance. Therefore, the laser beam used in the present invention has a wavelength which would not cause serious damages to the intrinsic properties of the substance. In the preferred embodiment, the wavelength of the laser beam ranges from 400 nm to 1500 nm. In the more preferred embodiment, the wavelength of the laser beam ranges from 830 nm to 1064 nm. Additionally, the laser beam used in the present invention has a power ranging from 1 mW to 100 mW, which is much lower than the 800 mW used in the dual-beam optical stretcher. Due to the lower frequency and power of the laser beam, the present invention can provide a relatively harmless approach for micromanipulating the biological substances.

In the oscillatory optical tweezers device provided in the present invention, the gain medium of the laser beam is Nd:YVO4. The solid state of Nd:YVO4 has physically stable atomic structure, broader and effective absorption spectrum, which is commonly used as a gain medium of laser beam.

The present invention further provides a method for trapping or stretching a microscopic substance comprising (a) providing a focused laser beam to form a focal spot and (b) scanning a plurality of points on said microscopic substance by said focal spot by way of the AOM. The scanning of step (b) is carried out in a back-and-forth or a circular pattern along a fixed direction. In the preferred embodiment, the focal spot formed in step (a) moves from one point to another on the microscopic substance. In addition, the scanning of step (b) has a frequency which would not cause serious damages to the intrinsic properties of said microscopic substance. In the preferred embodiment, the frequency of the scanning ranges from 1 Hz to 100,000 Hz. In the more preferred embodiment, the frequency of the scanning ranges from 10 Hz to 10,000 Hz. In the most preferred embodiment, the frequency of the scanning ranges from 100 Hz to 1,000 Hz. Furthermore, the duration of the scanning process is no more than 10 seconds per cell.

The scanning process in the present invention can be carried out in a continuous scanning mode or in a discrete scanning mode. In the continuous scanning mode, the focal spot formed in step (a) periodically moves between 2 or among more fixed points on the microscopic substance. In the discrete scanning mode, the focal spot periodically jumps between 2 or among more fixed points on the microscopic substance, causing the substance be stretched along the scanning direction.

The method provided by the present invention further comprises a step of imaging the microscopic substance. The imaging step is carried out by the CCD camera and computer system in the present invention. The CCD camera functions as a optical-electric signal converter and the computer system is for showing the image on a screen for real-time observation.

Following the imaging step the method provided by the present invention further comprises a step of measuring elongation of the stretched microscopic substance as a function of a scanned distance and correlating the data with a theoretical model for calculating the elastic constant of the microscopic substance.

The microscopic substances manipulated by the present invention include biological and non-biological substances such as human red blood cell, human T cell, human B cell, cancerous cell, liposome, or gold particle.

The method provided by the present invention can measure the mechanical properties of microscopic substance such as the elastic tension and deformability of cells. By comparing the above mechanical properties of cells, the cell type of an unknown cell can be identified.

By the novel oscillatory optical tweezers device and method provided in the present invention, the optical trapping and stretching of bi-concave and spherical human red blood cells as well as micron-size spherical liposome were demonstrated. The human red blood cells and liposome were trapped by a conventional stationary single-beam gradient-force optical trap and scanned the focal point of the trapping beam back-and-forth periodically along a fixed direction with an acousto-optic modulator. As the scanning distance gradually increased, the trapped particle was optically stretched along the scanning direction. This system provided a new platform to analyze soft-materials properties such as elasticity tension and deformability.

With an AOM, the optical field distribution can be tailored by applying a proper voltage signal to the AOM, and hence the deformation of the object can be altered. Optical trapping and stretching via oscillatory optical tweezers based on acousto-optic modulation thus provided a versatile platform for the study of either the steady-state or the dynamic visco-elastic property of microscopic substances including biological cells and other living biological samples.

A brief comparison of the oscillatory optical tweezers provided by the present invention with conventional one-beam optical tweezers and dual-beam optical stretcher was depicted in Table.1. The major disadvantages of the prior arts were listed in the gray ground.

TABLE 1

| The optical manipulation tools | Oscillatory optical tweezers (the present invention) | One-beam optical tweezers | Dual-beam optical stretchers |
| --- | --- | --- | --- |
| Laser beam used | Single, oscillatory | Single, fixed | Opposite two beams |
| Focusing of the laser beam | Highly focused but scattered | Highly focused | Non-focused |
| Potential damage | Low | High | Low |
| Power needed | Low (~10 mW) | Low | High (~800 mW) |
| Precision needed | Low | Low | High |
| Pretreatment | No need | No need | Need |
| Stability | High | High | Low |
| Use | Trapping and stretching | Trapping only | Trapping and stretching |

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

EXAMPLES

The following examples are offered by way of illustration and not by way of limitation.

Example 1

The Main Configuration of Oscillatory Optical Tweezers

A laser beam which causes optical trapping potential provided by the light source 10 (λ=1060 nm from a cw Nd:YVO4 laser) was sent into an AOM 20 (Isomet 1201E-2) at Bragg angle and subsequently expanded and collimated by a 2.5× beam-expander 30, consisting of a pair of lens in a telescopic arrangement. In addition, the telescopic beam-expander 30 also imaged the exit aperture of the AOM 20 onto the entrance aperture of a microscope object lens 40 (Olympus EA 100, N.A 1.25) such that angular scan of the beam at the output of the AOM 20 was transformed into a lateral displacement of the focal spot of the laser beam at the focal plane of the microscope object lens 40 without any beam walk-off at the entrance aperture. The direction of the diffracted output beam from the AOM 20 was controlled by applying different radio-frequency 21 (RF, 30-50 MHz) to the AOM 20. Both the frequency and the intensity of the RF 21 signal could be changed rapidly by changing the modulation voltage VT 22 and VMOD 23 (where VT 22 controlled the diffraction angle of the laser beam while VMOD 23 controlled the relative diffraction efficiency). An incoherent light source 50 illuminated the sample on the stage 60 from the backside for incoherent image of the trapped cell by a CCD camera 70 (752×582 pixels, WAT-100N).

Example 2

Trapping and Stretching of a Human RBC by the Oscillatory Optical Tweezers

A human RBC which was osmotically swelled into spherical shape was trapped by the oscillatory optical tweezers provided in the present invention. A sinusoidal voltage was applied to the AOM 20 through the $V_T$ 22 channel to scan the focal spot of the trapping beam; the scanning distance of the focal spot was fixed at 9.4 microns while the scanning frequency was varied from 1 Hz to 1 kHz in 4 steps (i.e., with scanning frequency=1 Hz, 10 Hz, 100 Hz, and 1 k Hz). At very low frequency (~a few Hz), the RBC followed the focal spot of the oscillatory tweezers with very little deformation. At frequency on the order of a few hundred Hz or higher, the RBC failed to track the scanning beam and responded to the average optical field distribution by deforming into an ellipsoid. An incoherent image of a spherical RBC trapped in conventional stationary single-beam optical tweezers depicted in the left panel of FIG. 1, while that of the same RBC trapped and stretched into ellipsoidal shape in oscillatory tweezers with a fixed oscillation frequency of 1 k Hz and a fixed scanning distance of 9.4 microns was depicted in the right panel.

Example 3

Figure 4:
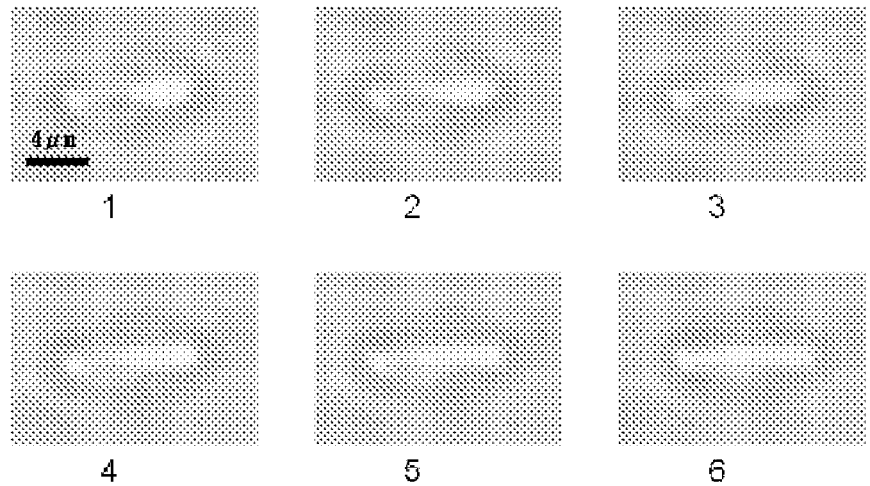
FIG. 4 indicates the side-view of a biconcave human RBC trapped and stretched by the oscillatory optical tweezers provided by the present invention where the focal spot (with optical power=12 mW) was discretely scanned at 100 Hz between two points. From (1) to (6), the distance between the two points was increased from 4.0 μm to 9.4 μm in steps of 0.9 μm.

Trapping and Stretching of a Spherical Liposome by Discrete and Continuous Scanning Mode Besides the continuous scanning mode described in example 1, one could also apply a square wave voltage to the AOM 20 to scan the beam in a discrete scanning mode where the focal spot of the beam jumped between two fixed points. The optical intensity distribution could be adjusted by adjusting the duty cycle of the square wave. A spherical liposome (diameter=3.42 μm) was trapped and stretched alternately with continuous and discrete scanning modes with the scanning distance varied from 0.72 μm to 2.88 μm in 0.72 μm step, and compared the deformation of the liposome at each scanning distance. The experimental results for the case when the scanning distance was 2.88 μm was depicted in FIG. 4 where the upper set of pictures was taken in the discrete scanning mode while the lower set was taken in the continuous scanning mode. In general, the continuous scanning mode caused smaller but more stable and more regular deformation, compared with the discrete scanning mode, due to more uniform force distribution on the sample.

Example 4

Figure 5:
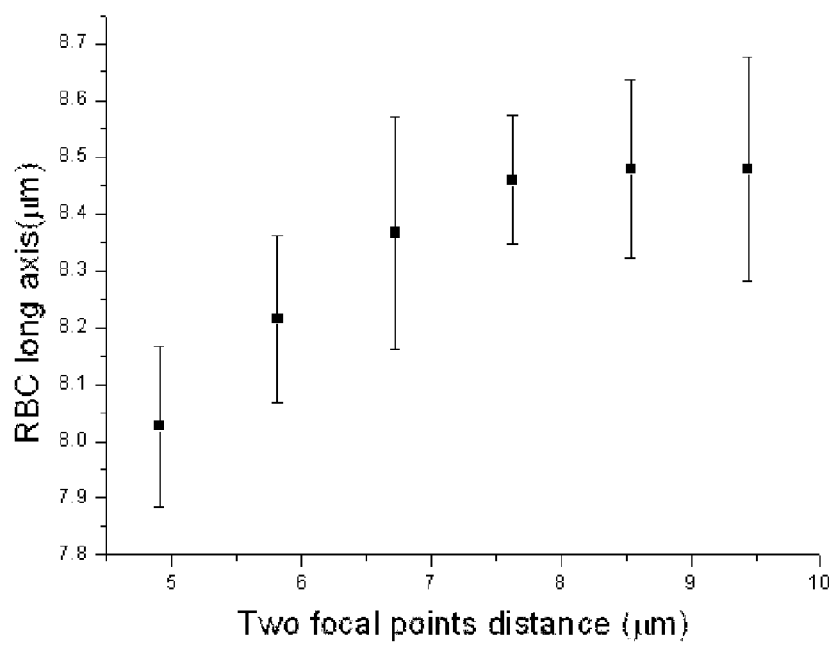
FIG. 5 indicates the stretched length of a biconcave human RBC as a function of the scanning distance, deduced from the images depicted in FIG. 4.

The Correlation of the Stretched Length of Biconcave RBC and the Scanning Distance A biconcave RBC was trapped and stretched by the oscillatory optical tweezers provided by the present invention. When a biconcave RBC sample was trapped in oscillatory optical tweezers, it flipped such that the platelet surface became parallel to the plane of the scanning trapping beam. We applied a 100 Hz square-wave voltage to the AOM 20 through the $V_T$ 22 channel to scan the focal spot of the laser beam and increased the amplitude step-by-step such that the distance between the two focal points varied from 4.0 μm to 9.4 μm in 0.9 μm step. The side-view of the elongated profile of the biconcave RBC in each step, as was imaged by the microscope object lens 40 on the CCD camera 70, was shown in FIG. 4, and the stretched length as a function of the scanning distance was plotted in FIG. 5. The stretched length at each step was measured by averaging over 9 frames of the CCD image which had been pre-calibrated. The trapping and stretching of RBC by this method thus resulted in a change in the diameter of a biconcave human RBC sample along the direction of scanning approximately from 8.0 μm to 8.5 μm. When the distance between the two focal spots was increased beyond 9.4 μm, the stretched length saturated at about 8.5 μm; besides, the trapping became unstable and the cell often escaped from the trap.

What is claimed is:

1. A device to trap or stretch a microscopic substance comprising:
    (a) a light source to irradiate laser beam;
    (b) an acousto-optic modulator (AOM) to regulate the direction of said laser beam irradiating from said light source;
    (c) a beam-expander to expand and collimate the light beam emitting from said AOM;
    (d) an object lens to focus the laser beam passing through said beam-expander to form a focal spot on the microscopic substance to trap or stretch the microscopic substance; and
    (e) an incoherent light source to image said microscopic substance through the object lens,
    provided that an interferometer is excluded.

2. The device as claimed in claim 1, wherein said AOM further regulates the scanning frequency or intensity of said laser beam.

3. The device as claimed in claim 1, which further comprises a Charge Coupled Device camera for imaging the microscopic substance.

4. The device as claimed in claim 1, which further comprises a computer for imaging the microscopic substance and processing the obtained data relating to said microscopic substance.

5. The device as claimed in claim 1, wherein said laser beam has a wavelength which would not cause serious damages to intrinsic properties of said microscopic substance.

6. The device as claimed in claim 5, wherein the wavelength of said laser beam ranges from 400 nm to 1500 nm.

7. The device as claimed in claim 1, wherein said laser beam has a power ranging from 1 mW to 100 mW.

8. The device as claimed in claim 1, wherein the gain medium of said laser beam is Nd: YVO4.

9. The device as claimed in claim 1, wherein said AOM is controlled by modulation voltage VT and VMOD.

10. A method for trapping or stretching a microscopic substance comprising:
 (a) providing a device of claim 1; and
 (b) providing a focused laser beam to form a focal spot and scanning a plurality of points on said microscopic substance by said focal spot by using the device of step (a).

11. The method as claimed in claim 10, wherein said scanning is carried out in a continuous mode or in a discrete mode.

12. The method as claimed in claim 10, wherein the frequency of said scanning ranges from 1 Hz to 100,000 Hz.

13. The method as claimed in claim 10, wherein the duration of said scanning is no more than 10 seconds per microscopic substance.

14. The method as claimed in claim 10, which further comprises a step of imaging said microscopic substance.

15. The method as claimed in claim 14, which further comprises a step of measuring elongation of said microscopic substance as a function of a scanned distance and correlating the data with a theoretical model for calculating the elastic constant of said microscopic substance.

16. The method as claimed in claim 10, wherein said microscopic substance is a human red blood cell, human T cell, human B cell, cancerous cell, liposome, or gold particle.

17. The method as claimed in claim 16, which measures the mechanical properties of said microscopic substance.

18. The method as claimed in claim 16, which measures the viscoelastic properties of cells.

19. The method as claimed in claim 16, which identifies the cell type of different cells.

* * * * *